United States Patent
Tanaka et al.

(10) Patent No.: US 6,866,875 B2
(45) Date of Patent: Mar. 15, 2005

(54) PINE CONE EXTRACTS AND USES THEREOF

(75) Inventors: Akiko Tanaka, St. Petersburg, FL (US); John Jessip, St. Petersburg, FL (US); William Guy Bradley, St. Petersburg, FL (US)

(73) Assignee: Tampa Bay Research Institute, St. Petersburg, FL (US)

( * ) Notice: Subject to any disclaimer, the term of this patent is extended or adjusted under 35 U.S.C. 154(b) by 0 days.

(21) Appl. No.: 09/964,240

(22) Filed: Sep. 26, 2001

(65) Prior Publication Data

US 2003/0072826 A1 Apr. 17, 2003

(51) Int. Cl.⁷ .................. A61K 35/78; A61K 45/00; A61K 47/00
(52) U.S. Cl. .................. 424/770; 424/776; 424/278.1
(58) Field of Search ................... 424/776, 770, 424/278.1

(56) References Cited

U.S. PATENT DOCUMENTS 4,985,249 A * 1/1991 Sakagami et al.
5,914,332 A * 6/1999 Sham et al.
5,929,047 A * 7/1999 Nakano

FOREIGN PATENT DOCUMENTS

CN         1279107     * 1/2001

OTHER PUBLICATIONS

Lai et al. AIDS Research and Human Retroviruses. 1990. vol. 6, pp. 205–217.*

Sakagami et al. Anticancer Res. 1991. vol. 11, pp. 881–888.*

* cited by examiner

Primary Examiner—Christopher R. Tate
(74) Attorney, Agent, or Firm—Pendorf & Cutliff

(57) ABSTRACT

A method of producing a pine cone extract and the pine cone extract produced there from, wherein the pine cone extract is useful in increasing the effects of nucleic acid vaccines and medicaments; and useful in the production of phenotypically immature and/or mature dendritic and/or fibrocyte cells.

19 Claims, 8 Drawing Sheets

PINE CONE EXTRACTS AND USES THEREOF

FIELD OF THE INVENTION

The present invention relates generally to the preparation of pine cone extracts, the pine cone extracts themselves and uses thereof, particularly as adjuvants in vaccination or treatment of vertebrates and as agents to promote differentiation of blood cells.

BACKGROUND OF THE INVENTION

As researchers gain an increased understanding of the vertebrate immune system, methods to harness and specifically employ the immune system in preventing and fighting of illnesses are constantly being sought. Because of the immune system's extraordinary versatility, this approach—in principle—offers the possibility to react on any substance of sufficient size. Numerous attempts have therefore been made to establish vaccination and/or immunological treatment methods of cancer, bacterial and viral infections.

Such therapy or vaccination methods commonly employ exposing the organism to be treated (in vivo treatment) to vaccine preparations of an antigenic substance, in order to generate an immune response. Particularly, the antigenic substance (antigen) is used to initiate production of immunoglobulins and/or cytotoxic phagocytic cells capable of detecting the antigenic substance itself or parts thereof (epitope), thereby becoming rapidly recognizable to the immune system. An antigen that has such becomes rapidly recognizable and can be inactivated or destroyed, e.g. by uptake into T cells and subsequent disintegration or by destruction of the cells comprising the antigen.

A similar method of vaccination or treatment is to extract lymphocytes—particularly lymphocyte stem cells—from the organism to be treated, exposing the extracted cells to the antigen, thus inducing production of immunoglobulins capable of detecting the antigen, and then reintroducing the immunoglobulin producing lymphocytes into the organism to be treated (ex vivo treatment).

The term "vaccination" denotes treatments of vertebrates primarily to prevent disease or ailment by creating, enhancing or maintaining the immune system's capacity to respond to antigens correlated with the disease or ailment. The term "treatment" denotes creating, enhancing or maintaining the immune system's capacity to respond to antigens correlated with a disease or ailment after the first onset of the disease or ailment, thus being therapeutic in nature. The active ingredient in a vaccination treatment is termed "vaccine", whereas the active ingredient in a therapeutic treatment is termed "medicament". The terms "vaccination" and "treatment" are used interchangeably, the same holds for the terms "vaccine" and "medicament".

One of the most important scientific discoveries of the last ten years has been the definition of tumor associated antigens (TAA) recognized by human T lymphocytes. For reviews see, e.g., Robbins and Kawakami "Human tumor antigens recognized by T cells", Current Opinion in Immunology 1996, 8:628–636; Rosenberg S A, "A new era for cancer immunotherapy based on the genes that encode cancer antigens", Immunity 1999, 10:281–287; Van den Eynde B J and van der Bruggen P, "T cell defined tumor antigens", Current Opinion in Immunology 1997, 9:684–693. The identification and molecular characterization of TAA is widely believed to have provided the means to create cancer vaccines. Current efforts in the creation of such vaccines are based on nucleic acid mediated immunization techniques, i.e. insertion of one or more antigen coding sequences (e.g. a TAA encoding sequence) into suitable expression (host) vectors capable of causing expression of the antigen coding sequence directly within transfected cells. The term "sequence" denotes hereinafter a nucleic acid characterized by the sequence of its nucleotides, wherein a nucleic acid is any molecule comprising one or more nucleotides selected from the group of adenine, guanine, cytosine, thymine, uracil or their functional equivalents like, for example, inosine and hypoxanthine, wherein each nucleobase is linked to a backbone comprising a pentose like ribose and/or deoxyribose, an other sugar or an amino acid, and wherein the individual backbones are linked/connected to one another by, for example, phosphodiester bonding, peptide bonding or other adequate means of linkage/connection. Examples of nucleic acids are deoxyribonucleic acid (DNA) and ribonucleic acid (RNA). Commonly employed host vectors are bacteria and viruses or bacterial and viral genomes, respectively. Recent studies have shown that a cellular or encapsulated vector is not always necessary for vaccine preparation. Immunization with "naked" plasmid DNA and/or with RNA, that is with the nucleic acid being devoid of any other structural components as proteins, lipids, or carbohydrates, can elicit powerful cellular and antibody responses. Nucleic acid vaccines, also termed recombinant vaccines, are thus vaccines in which the genome of the host vector integrates a—frequently heterologous—nucleic acid sequence coding for an immunogen (antigen).

Compared to cell-based vaccines or cell lysates, recombinant vaccines have multiple advantages, the most prominent is probably that they can focus the immune response against a single, specific antigen like a TAA, and thus limit the possibility of releasing an uncontrolled autoimmune aggression against hitherto unknown antigens being present in normal tissues and tumor cells.

Currently vaccination and therapeutic success vary greatly for different ailments and even among patients treated for the same ailment. Furthermore, vaccination does not always last satisfactorily long but can wear off within weeks. These drawbacks hold true also for a number of other vaccination methods, which may in particular involve administration of live or inactivated vaccines. In general, vaccines are not always able to generate an appropriate and effective immune response by themselves.

Certain substances, when administered simultaneously with a specific antigen, will enhance the immune response to that antigen. Such substances (adjuvants) are routinely included in inactivated or purified antigen vaccines. Examples of adjuvants in common use are aluminium salts, liposomes and immunostimulating complexes (ISCOMS), complete and incomplete Freund's adjuvant, muramyl di-peptide and cytokines like interleukin (IL) 2, IL-12 and interferon (IFN) gamma.

Yet, while some adjuvants are well suitable in combination with specific antigens or vaccines, they may fail in other combinations, or they may be toxic themselves to vertebrates like humans, promote poor cell mediated immunity, are unstable or are expensive and/or cumbersome to prepare.

Improved methods for vaccination and treatment of illnesses and ailments in vertebrates are therefore extremely useful.

Another aspect is that for purposes of science, generation of specific cell types e.g. for tissue culture purposes is frequently needed. Among the cell types needed for investigation are dendritic cells and recently discovered fibrocytes.

Dendritic cells are potent antigen presenting cells. They are also reported to act as stimulators of a mixed lymphocyte reaction, to migrate selectively through tissues, to take up, process and present antigens, and serve as passenger cells that elicit rejection of transplanted tissues. For a review see for example Hart DNJ "Dendritic cells: unique leukocyte populations which control the primary immune response", Blood, 1997, 90:3245–3287. Clearly, the study of dendritic cells offers potential applications in any field where the correct recognition of antigens and generation of immune responses is desirable. Such fields are, for example, transplantation medicine, vaccination, therapy of cancer and other illnesses connected with antigen presentation, prevention and treatment of autoimmune diseases and the like, see for example Dallal R M and Lotze M T, "Dendritic cells and human cancer vaccines", Current Opinion in Immunology, 2000, 12:583–588. However, understanding of dendritic cells and their differentiation is insufficient. It is therefore desirable to have methods for producing dendritic cells.

Current protocols for the production of dendritic cells rely on their differentiation from peripheral blood mononuclear cells, bone marrow cells or other $CD34^+$ cells by exposing such cells to multiple cytokine combinations including granulocyte-macrophage colony stimulating factor (GM-CSF), stem cell factor (SCF), tumor necrosis factor alpha (TNFα), tumor growth factor beta (TGFβ) and IL-4. For a review see for example Strunk D et al., "Generation of human dendritic cells/Langerhans cells from circulating CD34+ hematopoietic progenitor cells", Blood, 1996, 87:1292–1302 and Soligo D et al., "Expansion of dendritic cells derived from human $CD34^+$ cells in static and continuous perfusion cultures", British Journal of Hematology, 1998, 101:352–363. Likewise, dendritic cells have been produced from $CD14^+$ blood monocytes and different maturation stages have been described. For a review see Winzler C et al., "Maturation stages of mouse dendritic cells in growth factor-dependent long-term cultures", Journal of Experimental Medicine, 1997, 185:317–328 and U.S. Pat. No. 6,194,204 B1 by Crawford and Chester. Yet, present protocols rely on expensive and unstable cytokine media components. Likewise, the yield of present protocols for the production of dendritic cells is often considered unsatisfactorily low.

Fibrocytes are a recently described type of cell characterized by their distinct phenotype (collagen+, $CD34^+$), which normally is also vimetin+, $CD13^+$ and $CD45^+$. They are reported to enter rapidly from blood into subcutaneously implanted wound chambers. They are also frequently present in connective tissue scars and may play an important role in wound repair and pathological fibrotic responses. For a review see for example Bucala R et al., "Circulating fibrocytes define a new leukocyte subpopulation that mediates tissue repair", Mol. Med. 1994, 1:71–81, and Chesney J and Bucala R, "Peripheral blood fibrocytes: novel fibroblast-like cells that present antigen and mediate tissue repair", Biochemical Society Transactions, 1997, 25:520–4. Like dendritic cells, protocols for the production of fibrocytes rely on expensive and unstable cytokine media components and provide often unsatisfactorily low yields. Therefore, it can be appreciated that there exists a continuing need for new treatments of illnesses and ailments in vertebrates, which can be used to harness and employ the vertebrate immune system in preventing and fighting illness and ailments which remains unsolved by the prior art. Further, there is a need for new methods of generating specific cell types for scientific use. In this regard, the present invention fulfills this need.

SUMMARY OF THE INVENTION

It is thus an object of the invention to provide novel methods and substances for vaccination and/or treatment, particularly to improve and enhance the effects of nucleic acid vaccines and medicaments. The methods and substances to be provided by the invention should be applicable for a wide spectrum of vaccination and treatment purposes. The substances and methods according to the object of the invention should have low or no toxicity to the treated vertebrate or healthy cells, tissues and organs of such vertebrate. The substances should be easy to prepare, stable and inexpensive. The methods of vaccination and/or treatment should also be easy to perform and not require expensive additional equipment.

It is another object of the invention to provide substances and methods for the preparation of cells with dendritic and/or fibrocyte like phenotype. The substances should be easy to prepare, stable and inexpensive. The methods should have a high yield of at least one of these cell types. They should also be easy to perform and not require expensive additional equipment.

The inventors have now found that pine cone extracts have excellent adjuvant properties when combined with vaccines or medicaments for immunotherapy. The inventors have also found that pine cone extracts can induce differentiation of a number of cell types into cells with a phenotype of immature and/or mature dendritic and/or fibrocyte cells. The inventors have also found that a fraction of pine cone extracts is particularly useful for achieving the above objects.

It is the object of the invention to provide a method for the production of a pine cone extract. It is a further object of the invention to provided a pine cone extract produced by that method.

Another object of the invention is to provide systems for vaccination and/or therapy of vertebrates including a kit that has a vaccine and an adjuvant or a medicament and an adjuvant; and providing methods for administering the vaccinating and/or treating to a vertebrate.

An even further object of the present invention is to provide a method for producing phenotypically immature and/or mature dendritic and/or fibrocyte cells.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying examples and descriptive matter in which there is illustrated the preferred embodiments of the invention.

BRIEF DESCRIPTION OF THE DRAWINGS

The invention will be better understood and objects other than those set forth above will become apparent when consideration is given to the following detailed description thereof. The figures show.

DETAILED DESCRIPTION OF THE INVENTION

Figure 1:
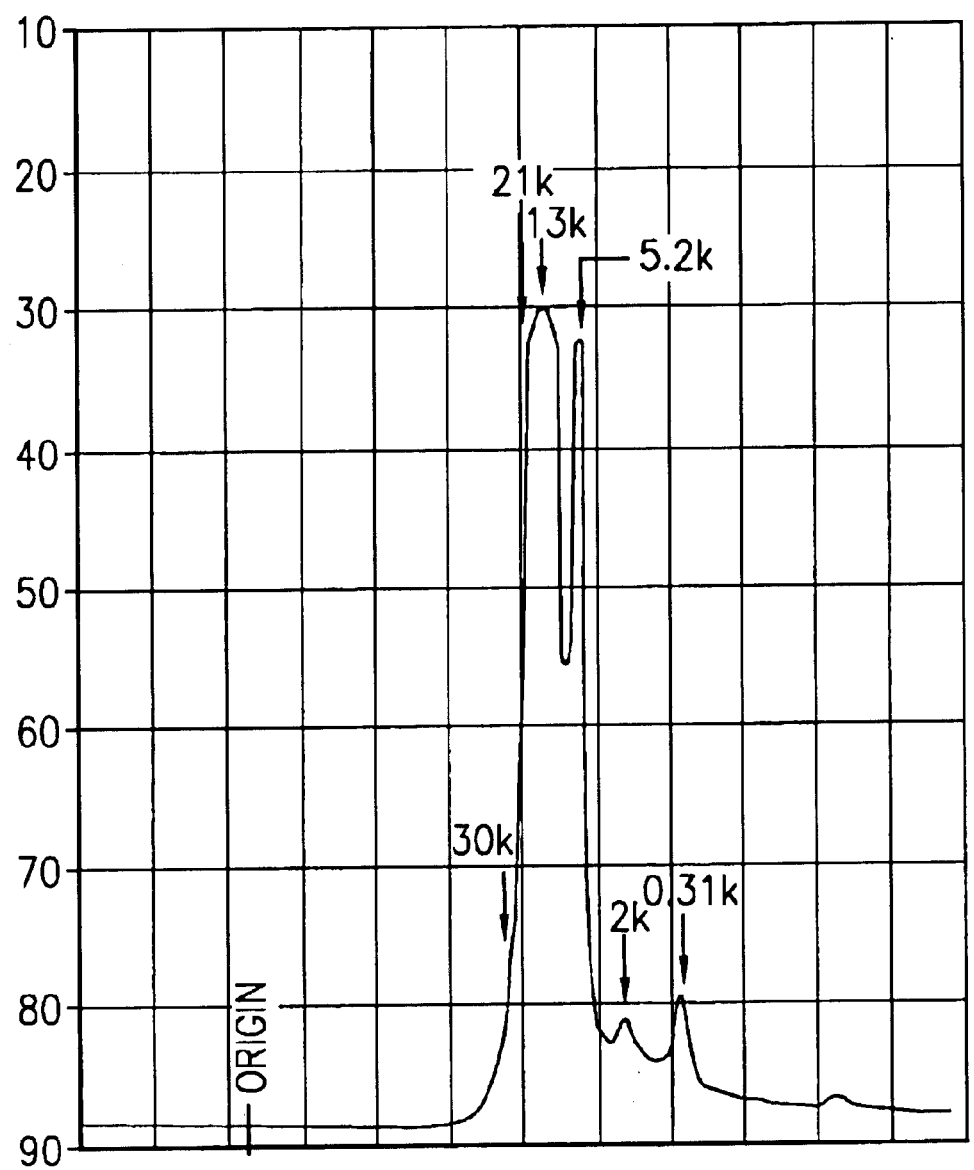
FIG. 1: Fast protein liquid chromatography (FPLC) spectrum of the pine cone extract of method 1.

Plants have been a major source of medicinal compounds for thousands of years. Chemical components and analogs which have been derived from plant materials now comprise a major portion of the medicines in clinical use. One such plant product is derived from the pine cones of various pine trees.

Pine cone extracts have been known before. Sakagami H et al. report in "Antitumor, antiviral and immunopotentiating activities of pine cone extracts: potential medicinal efficacy of natural and synthetic lignin-related materials", Anticancer Research, 1991, 11:2881–2888 that crude water extracts of pine cones comprise substances with the potential to induce differentiation of human myeloblastic leukemic ML-1 cells into macrophage like cells. The differentiation inducing substance reportedly migrated very fast on polyacrylamide gel and could not be recovered in a useful amount.

Besides crude water-based extracts, Sakagami et al. describe in the same publication methods of preparation and fractionation of pine cone extracts. The pine cone extracts are prepared by repeated hot water extraction of *Pinus parviflora* Sieb. et Zucc. cones and subsequent ethanol precipitation. They also report that certain fractions of thus prepared pine cone extracts could prolong survival of mice transplanted with ascites sarcoma-180 cells and BALB/c mice transplanted with ascites Meth A fibrosarcoma. Sakagami et al. also report that the active components of pine cone extracts are lignins. Furthermore, they conclude that natural and synthetic lignins can have immunopotentiating capacity. Sakagami et al. also suggest that the immunopotentiating capacity is mediated at least partially through T-cell activation, although activation of cell populations other than T-cells and subsequent activation of T-cells is also said to be a possible way of activation.

U.S. Pat. No. 4,985,249 (Sakagami, Konno and Nonoyama) discloses the use of pine cone extract as anti-HIV agents. Chinese patent abstract CN 1279107 (Xin Yaolu) discloses a medicine for treating AIDS and cancers prepared from castor, phytolacca root, liquorice root and pine cone through extracting phytolaccatoxin, phytolaccapolyose, ricin, glycyrrhizic acid for injection and pineal acidic polyose and preparing them into injection and slow releasing capsules. Chinese patent abstract CN 1122206 (Xiyun Sun and Yinglong Wang) disclose a low-salt soy sauce produced through solid fermentation, featuring a pine nut kernel preparation and Xianggu mushroom extract preparations as supplements added into soy sauce. The soy sauce such produced is reported to have certain cancer-preventing and curing health functions.

Yet, the above references do not disclose immunostimulating properties of pine cone extracts in general nor do they disclose the methods for the production of immature and/or mature dendritic and/or fibrocyte cells. It is the merit of the inventors to have established usefulness of pine cone extracts in such applications.

As far as the present invention is concerned, useful pine cones can be of any species and variety of genus *Pinus*, especially those of table 1, without intended limitation to the correctness of the taxonomical classification of that table. Preferred pine cones are those of *P. taeda* (loblolly), *P. elliottii* (slash), and *P. palustris* (long leaf). The inventors have found that pine cones in general and pine cones of the preferred species in particular contain substances and compositions (active ingredients) useful in vaccination and/or therapy methods and likewise comprise substances and compositions useful for the production of dendritic and/or fibrocyte cells. They have also found that, contrary to the suggestion of Sakagami et al. (supra), the lignin fraction of pine cone extracts is necessary but not sufficient for satisfactory adjuvant properties of pine cone extracts, particularly in nucleic acid vaccination and/or treatment methods.

TABLE 1

Pines producing pine cones useful for preparing pine cone extracts

| | |
|---|---|
| Subgenus *Pinus* | |
| Section *Pinus*, Subsection *Pinus* | *P. densata, P. densiflora, P. heldreichii, P. hwangshanensis, P. kesiya, P. luchuensis, P. massoniana, P. mugo, P. nigra, P. resinosa, P. sylvestris, P. tabuliformis, P. thunbergii, P. tropicalis, P. yunnanensis* |
| Section *Pinea*, Subsection *Pinaster* Loudon | *P. brutia, P. canariensis, P. halepensis, P. latteri, P. merkusii, P. pinaster, P. roxburghii* |
| Section *Pinea*, Subsection *Pineae* Little & Critchfield | *P. pinea* |
| Section *Trifoliis*, Subsection *Contortae* Little & Critchfield | *P. banksiana, P. contorta* |
| Section *Trifoliis*, Subsection *Australes* Loudon | *P. caribaea, P. clausa, P. cubensis, P. echinata, P. elliottii, P. glabra, P. occidentalis, P. palustris, P. pungens, P. rigida, P. serotina, P. taeda, P. virginiana* |
| Section *Trifoliis*, Subsection *Ponderosae* Loudon | 'Sabinianae Group': *P. coulteri, P. sabiniana, P. torreyana* 'Ponderosa Group': *P. arizonica, P. durangensis, P. engelmannii, P. jeffreyi, P. ponderosa, P. washoensis* 'Montezumae Group': *P. devoniana, P. hartwegii, P. montezumae* 'Pseudostrobus Group': *P. douglasiana, P. maximinoi, P. pseudostrobus* |
| Section *Trifoliis*, Subsection *Oocarpae* Little & Critchfield | 'Attenuata Group': *P. attenuata, P. muricata, P. radiata* 'Oocarpa Group': *P. greggii, P. jaliscana, P. oocarpa, P. patula, P. praetermissa, P. pringlei, P. tecunumanii* 'Teocote Group': *P. herrerae, P. lawsonii, P. teocote* |
| Section *Trifoliis*, Subsection *Leiophyllae* Loudon | *P. leiophylla, P. lumholtzii* |
| Subgenus *Ducampopinus* | |
| Section *Ducampopinus*, Subsection *Krempfianae* Little & Critchfield | *P. krempfii* |
| Section *Gerardiana*, Subsection *Gerardianae* | *P. bungeana, P. gerardiana, P. squamata* |

TABLE 1-continued

Pines producing pine cones
useful for preparing pine cone extracts

| | |
|---|---|
| Loudon | |
| Section *Parryana*, | *P. nelsonii* |
| Subsection *Nelsoniae* | |
| Van der Burgh | |
| Section *Parryana*, | *P. maximartinezii, P. pinceana,* |
| Subsection | *P. rzedowskii* |
| *Rzedowskianae* | |
| Carvajal | |
| Section *Parryana*, | *P. cembroides, P. culminicola,* |
| Subsection *Cembroides* | *P. discolor, P. edulis,* |
| Engelmann | *P. johannis, P. juarezensis,* |
| | *P. monophylla, P. orizabensis,* |
| | *P. remota* |
| Section *Parryana*, | *P. aristata, P. balfouriana,* |
| Subsection *Balfourianae* | *P. longaeva* |
| Engelmann | |
| Subgenus *Strobus* | |
| Section *Strobus*, | *P. amamiana, P. armandii,* |
| Subsection *Strobi* | *P. ayacahuite, P. bhutanica,* |
| Loudon | *P. chiapensis, P. dalatensis,* |
| | *P. fenzeliana, P. flexilis,* |
| | *P. lambertiana,* |
| | *P. monticola, P. morrisonicola,* |
| | *P. parviflora, P. peuce, P. pumila,* |
| | *P. strobiformis, P. strobus,* |
| | *P. wallichiana, P. wangii* |
| Section *Strobus*, | *P. albicaulis, P. cembra,* |
| Subsection *Cembrae* | *P. koraiensis, P. sibirica* |
| Loudon | |

One aspect of the present invention is providing a method for producing a pine cone extract. This method can be divided into two phases, hereinafter termed method 1 and method 2.

Method 1 requires heat extraction of defatted ground pine cone material with an aqueous solvent that contains potassium hydroxide. Once the pine cone material is extracted, particulate matter with an average particle size greater than 0.2 µm is removed. A resulting aqueous solution is obtained (supernatant), which has its pH adjusted to be between 6.0 and 8.0 to obtain the extract of method 1.

Method 2 uses the extract (supernatant) obtained by method 1. In method 2, the extract of method 1 (a solution) is subjected to further filtration to obtain a retentate fraction. By way of the centrifugal filtration process the particulate matter of smaller than 30 kDa is removed. What remains is particulate matter greater than 30 kDa on top of the filter, this retentate fraction is pine cone extract of the preferred method (method 2).

For the purpose of the above method, the pine cones can be in the form of shredded pine cone material. Such pine cone material is preferred because it facilitates subsequent extraction. It is also easily commercially available and maintains sufficiently stable and uniform composition throughout several batches.

Prior to use in the above method according to the invention, pine cones can be cleaned. This can be preferably done by washing the pine cones (or pine cone material) with deionized water.

The pine cones (or pine cone material) are defatted prior to aqueous extraction. Defattening is preferably achieved by washing the pine cones with ethanol and subsequent drying of the washed cones or shreds. The defatted pine cones can be stored at room temperature in a closed container.

The defatted pine cones are preferably ground into small particles prior to the extraction step. This treatment facilitates release of active ingredients. Preferably the particle size should be in the range of 80–120 mesh.

The solvent for heat extraction of the pine cones is an aqueous solution comprising potassium hydroxide (KOH). The solution comprises at least 0.25% w/w potassium hydroxide, preferably it comprises 0.5–2% w/w potassium hydroxide, more preferably it comprises 1% w/w potassium hydroxide. The inventors have found that with these concentrations of potassium hydroxide, particularly effective extracts can be obtained. The pH of the solvent is preferably at least 8, more preferably at least 10, most preferably in the range of 11–13.

Extraction of the pine cone material is performed by adding solvent to the pine cones and heating the mixture, preferably to temperatures at or above 80° C. (176° F.). The inventors have found that extraction can be performed conveniently fast and with sufficient extraction rates when the solvent is boiling. It is particularly preferred to extract the pine material by autoclaving, that is at 121° C. This way a particularly fast, gentle and complete extraction of the active ingredients can be achieved.

After extraction it is convenient to allow the mixture to cool, preferably to room temperature. If necessary, the mixture can be stored in a refrigerator for 12 hours before further processing.

Particulate matter with average particle sizes greater than 0.20 µm is then removed from the mixture. This can be achieved by any particle separation method. The inventors have found that a particularly convenient and efficient way is a two step process, wherein in the first step coarse particulate matter is removed by filtration, the remaining unwanted particulate matter is then removed by centrifugation, preferably at 4° C. ±2 C.

The resulting particle-depleted mixture is then treated to adjust the pH to between 6.0 and 8.0. This is preferably done by titration with 1 N HCL until the pH of the mixture is 7.0. The mixture can then be distributed into packaging units.

The mixture can be sterilized after adjustment of pH. It is preferred to sterilize by autoclaving at 121° C., liquid cycle, for 20 minutes. Other sterilization techniques can also be applied, like irradiation and the like.

The mixture (PCE of method 1) can be stored after pH adjustment and optional sterilization. Long term storage stability is best ensured by storage at low temperatures, preferably at or below 4° C., even more preferably in a frozen state, most preferably at −20° C. It is, however, preferred not to store the mixture at all but to use it immediately.

After pH adjustment and optional sterilization of the above extract is subjected to futher filtration to remove material smaller than 30 kDa, using Millipore Ultrafree Centrifugal concentrators (Ultrafree-15, 30,000 mw cutoff). It is preferred to centrifuge at 2000×g for 60 min to filter the solution and recover the retentate fraction with an average molecular mass no less than 30 kDa.

The retentate fraction containg an average molecular mass greater than 30 kDa is then returned to its original volume using aqueous 10 mM potassium hydroxide solution at a pH between 6.0 and 8.0. It is particularly preferred to return the retentate fraction in aqueous 10 mM potassium hydroxide solution, pH 7.0. The volume of potassium hydroxide solution can be adjusted according to the desired concentration of retentate fraction.

The solution can finally be sterilized, preferably by filtration with a 0.2 µm filter. Other sterilization techniques may likewise be applied.

The resulting pine cone extract of method 2, viz the further filtration and optionally sterilized concentrate, is then ready to be used.

Another aspect of the invention provides a system for vaccination and/or therapy. Vertebrates eligible for the treatment or vaccination are any vertebrates. Preferred vertebrates are mammals including humans, apes, dogs, cats, rabbits, goats, guinea pigs, hamsters, cows, horses, sheep, mice and rats. The general properties of the immune system of these vertebrates are similar enough so that experimental findings in one species can be interpolated with reasonable confidence to other species as well.

The system for vaccination and/or therapy includes a composition or a kit comprising a) a vaccine or medicament and b) an adjuvant, wherein the adjuvant comprises a pine cone extract.

The inventors, having recognized the usefulness of pine cone extracts as adjuvants, have furthermore found out that the beneficial adjuvant effect of pine cone extracts is not dependent on the simultaneous administration of vaccine and pine cone extract. The pine cone extract can be administered to the vertebrate before, during, simultaneously with or after administration of the vaccine or medicament. The inventive system for vaccination and/or therapy is therefore not limited to compositions comprising both vaccine and pine cone extract, but can also be a kit comprising, as separate entities, the vaccine, optionally also comprising a pine cone extract, and the pine cone extract. A composition comprising vaccine and/or medicament and a pine cone extract is particularly useful for simultaneous administration of both ingredients to the vertebrate to be treated. The kit allows for the independent administration of vaccine (or medicament) and pine cone extract. The kit is therefore particularly suitable if administration of the pine cone extract to the vertebrate is to start before administration of the vaccine.

Preferably, the vaccine or medicament is a nucleic acid vaccine or medicament. The inventors have found that pine cone extracts are particularly effective as adjuvants in nucleic acid vaccination or treatment methods. With nucleic acid vaccines and/or medicaments a particularly high degree of immunization of activation of the immune system can be achieved when used with a pine cone extract adjuvant.

In a further preferred method of the invention, the pine cone extract comprises a pine cone extract produced by method 1 (supra), that is by heat extraction of defatted ground pine cone material with an aqueous solvent containing potassium hydroxide, then removing particulate matter with an average particle size greater than 0.2 $\mu$m, and finally adjusting the pH of the resulting solution to between 6.0 and 8.0.

Pine cone extracts prepared in this way have particularly strong effects in vaccination and therapeutic applications. It is preferred to use these pine cone extracts in adjuvants with nucleic acid vaccines or medicaments, as such pine cone extracts offer strong immunoactivating properties and offer the advantage of increasing the immune response resulting from the vaccine or medicament. For preferred modes of manufacturing such pine cone extracts see above.

A particularly preferred embodiment of the kit or composition of the invention is one wherein the pine cone extract comprises a pine cone extract produced by method 2. It has turned out that such pine cone extract, being in effect the fraction of molecules with 30 kDa or more of the pine cone extract obtained by method 1, comprises essentially all immunoactive ingredients required for stimulating the immune system or, in ex vivo or in vitro applications, the cells required in mediating the immune response to the antigen of the vaccine or medicament.

The invention also provides a method of vaccinating or treating a vertebrate, wherein the vertebrate is administered a vaccine or medicament. After administration of the vaccine or medicament, the vertebrate is administered a pine cone extract.

Such method offers the advantages of pine cone administration at vaccination and/or therapy as previously mentioned.

Administration of both vaccine and pine cone extract can be accomplished in various ways. Among these are oral and anal administration, cutaneous application, subcutaneous injection, intramuscular injection and intravenous injection. Injection can be accomplished using syringe systems or devices commonly termed "particle guns". The mode of administration of the vaccine or medicament is chosen in accordance with the nature of the vaccine or medicament. While some vaccines achieve high immunization levels by intramuscular injection, others are preferentially administered orally.

It is preferred to administer the pine cone extract orally or by intramuscular injection. Both modes of administration offer a particularly pronounced immunostimulating effect of the pine cone extract, augmenting its adjuvant properties.

For the reasons detailed above, in preferred embodiments the vaccine or medicament comprises a nucleic acid vaccine or medicament.

Further, the pine cone extract administered to the vertebrate with the vaccine or medicament is preferably a pine cone extract produced by method 1.

Such administration, particularly in combination with nucleic acid vaccines or medicaments, effectively exploits the advantages of the special pine cone extract as described above.

It is particularly preferred that the pine cone extract comprises a pine cone extract produced by method 2. The advantages of this pine cone extract have been described above. In combination with nucleic acid vaccines and/or medicaments, such pine cone extracts can provide a particularly long lasting, strong vaccination and/or a rapid or expedited alleviation of illness/ailment.

According to another aspect the invention provides a method for producing phenotypically immature and/or mature dendritic and/or fibrocyte cells, which method comprises exposing cells selected from the group of blood mononuclear cells, thymocytes, splenocytes, umbilical cord blood cells, bone marrow cells, $CD34^+$-cells, $CD14^+$-cells or mixtures thereof to an effective amount of a pine cone extract.

The inventors have found that pine cone extracts have a pronounced effect on the differentiation process of cells of the immune system. In particular, they established that pine cone extracts can induce differentiation to phenotypically immature and/or mature dendritic cells and fibrocytes. The invention now enables achieving a particularly high yield of cells having differentiated into immature and/or mature dendritic cells. Such high yields could not be established previously by common methods of induction of differentiation, e.g. doses of cytokines.

Differentiation can be advantageously enhanced by further exposing the selected cells or the selected mixture to $CD3^+$-cells.

Preferably, the pine cone extract used to achieve a high yield of immature and/or mature dendritic and/or fibrocyte cells is produced by method 1. Such pine cone extracts are particularly effective in inducing the desired differentiation into phenotypically immature or mature dendritic cells and/or fibroblasts. This method of differentiation can be advantageously combined with exposure to CD3$^+$-cells to achieve and maintain a high yield of differentiation.

It is particularly preferred that the pine cone extract be obtained by method 2. Such method exploits the advantages inherent in this pine cone extract as described above.

EXAMPLE 1

Preparation of a Pine Cone Extract According to Method 1

This example illustrates the production of pine cone extracts (PCE) according to method 1.

Commercially available shredded pine cone material from International Forest Company such as, loblolly pine, slash pine and long leaf pine is used. 5 kg of the shredded pine cone material is washed twice in about 10 l of deionized water. The washed pine cone material is then defatted by briefly washing it in 10 l of 95% ethanol while agitating. The pine cone material is air dried over night and can be stored at room temperature (18–25° C.) if not used immediately.

The cleaned and defatted pine cone material is ground to a particle size of approximately 80–120 mesh in a blender. Of this ground material, 600 g are placed in a 20 l spinner flask. 4.5 l of 1% w/w aqueous potassium hydroxide solution are added. The opening of the flask is plugged with a cotton ball wrapped with cheesecloth. The flask is then autoclaved for 1 h with slow exhaust at 121° C. under liquid cycle conditions. After autoclaving, the flask is allowed to cool off. If its contents are not immediately processed further, the flask can be stored in a refrigerator at 4° C.

Large particles are filtered out of the autoclaved suspension with a nylon mesh filter on a Buchner funnel attached to a suction flask with vacuum applied thereto. Fine particles are removed by centrifuging the filtrate in a Beckman medium speed centrifuge using a JA-10 rotor and corresponding bottles, centrifuging at 8000 rpm for 10 min at 4° C. The supernatant is taken off and processed further.

The pH of the centrifugation supernatant (extract) is adjusted to 7.0 by adding 1 N aqueous hydrochloric acid. A control sample of 10 ml of the neutralized supernatant is retained.

The neutralized extract is distributed into 500 ml glass bottles (approx. 400 ml per bottle). If not used immediately, the extract is stored in a refrigerator. The extract is sterilized by autoclaving for 20 min at 121° C. under liquid cycle conditions. After cooling, the autoclaved extract (extract according to method 1) is ready to be used. It can be stored in a refrigerator.

EXAMPLE 2

Preparation of a Pine Cone Extract According to Method 2 from the Pine Cone Extract of Example 1

This example illustrates the production of pine cone extracts according to method 2.

15 ml of the pine cone extract of example 1 is placed in a sterile 50 ml conical polypropylene centrifuge bottle (Millipore Ultrafree-15 centrifugal concentrator, Fisher cat. no. UFV2 BTK 10) and centrifuged for 1 h at 2000×g (Eppendorf model 5810R centrifuge) (room temperature to 4° C.). The retentate fraction is drawn off and saved. The filtrate, containing molecules smaller that 30 kDa is discarded.

The retentate fraction is suspended in 10 mM aqueous potassium hydroxide buffer at pH 7.0 to produce a final extract volume of 15 ml.

The suspended retentate fraction (extract method 2) is sterilized by vacuum filtration with a 0.2 μm filter (Nalgene PES membrane, cat. no. 124-0020).

The sterilized pine cone extract of method 2 is then ready to be used. It can be stored in a refrigerator.

EXAMPLE 3

Properties of the Pine Cones of Examples 1 and 2

This example illustrates the properties of pine cone extracts according to methods 1 and 2.

Figure 2:
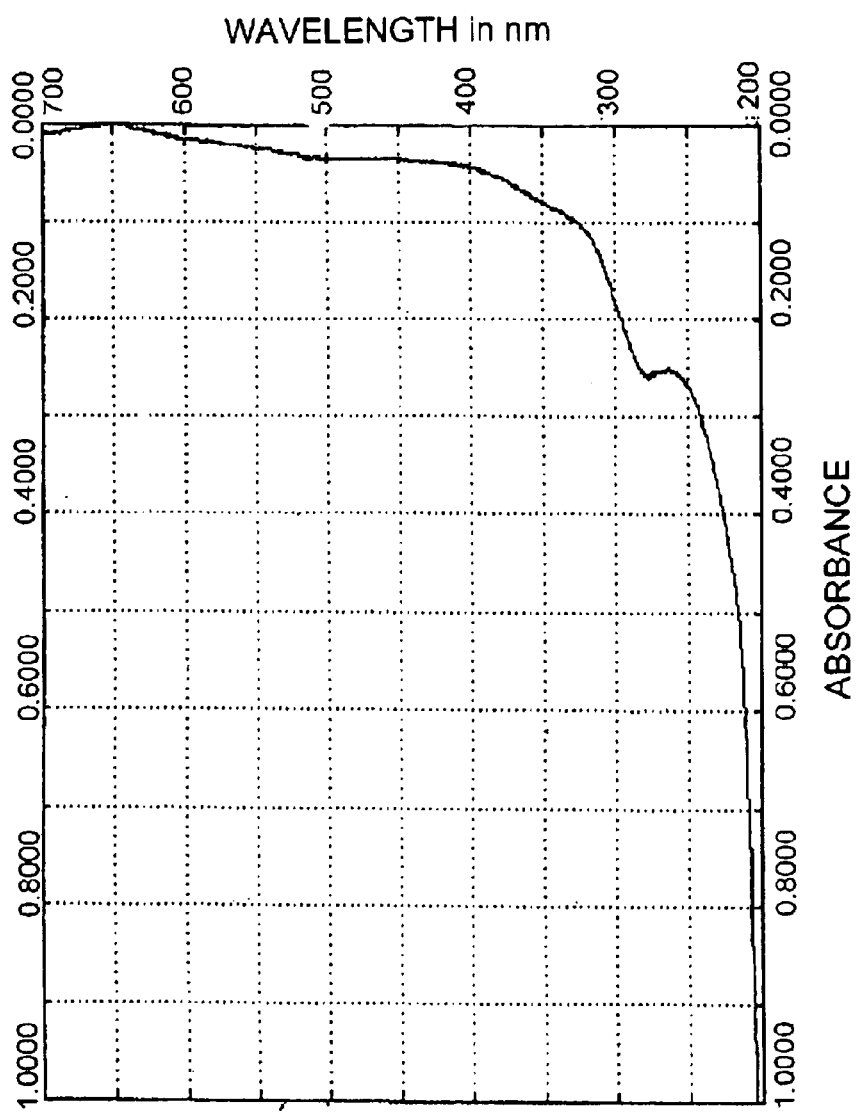
FIG. 2: Absorption spectrum of the pine cone extract of method 1.

The pine cone extracts of methods 1 and 2 are brown liquids. They are miscible with water, with mixtures of water and ethanol and with acetone. They comprise polysaccharides and polyphenylpropenoids. The molecular weights of the main components are given in table 2. A fast protein liquid chromatography (PFLC) spectrum of the pine cone extract of method 1 is given in FIG. 1. An UV/VIS absorption spectrum of the pine cone extract of method 1 is given in FIG. 2.

TABLE 2

Molecular weights of pine cone extract main components

| Component nr. | Extract of method 1 [kDa] | Extract of method 2 [kDa] |
|---|---|---|
| 1 | >30 | >30 |
| 2 | 21.0 | — |
| 3 | 13.5 | — |
| 4 | 3.6 | — |
| 5 | 2.1 | — |

EXAMPLE 4

Preparation of Peripheral Blood Mononuclear Cells

This example illustrates the preparation of peripheral blood mononuclear cells (PBMC).

Peripheral blood mononuclear cells are isolated from buffy coats. Buffy coats are the retrieved white cell layer after centrifugation of donated units of whole blood. The PBMC are harvested over a density gradient (Histopaque 1.077, Sigma Chemical Company). The PBMC are recovered from the gradient and washed with phosphate buffered saline (PBS, see Sambrook J C et al., "Molecular Cloning: A Laboratory Manual", Cold Spring Harbor Laboratory Press 1989), pH 7.4. After washing, the cells are suspended in an augmented RPMI 1640 complete medium comprising standard RPMI 1640 medium as defined in Moore, G E, Gerner, R E, and Franklin, H A (1967) A.M.A. Vol. 199, page 519, and additionally 10% fetal calf serum, 100 units/ml penicillin, 100 μg/ml streptomycin and 50 μM 2-mercaptoethanol. The final cell concentration is adjusted to be 2×10$^6$ cells/ml. Of these, CD14$^+$ and CD3$^+$ cells were isolated with CD14 or CD3 microbeads (Miltenyi Biotech, Auburn, Calif.), respectively, according to the manufacturer's instructions. The isolated cells are checked to be more than 95% CD14$^+$ and CD3$^+$, respectively, as determined by immunofluorescent staining.

EXAMPLE 5

Exposition of PBMC with Pine Cone Extracts

This example illustrates morphological changes induced by exposition of PBMC to pine cone extracts.

PBMC of example 4 with a cell concentration of $2 \times 10^6$ cells/ml in augmented RPMI 1640 medium (medium definition as in example 4) are distributed to the wells of 96 well flat-bottom microtitration plates (Nunc) with 100 µl cell suspension per well. Pine cone extracts of methods 1 and 2 (examples 1 and 2, respectively) are added to each well to a final concentration of 0, 6.25, 12.5, 25, 50, 100 and 300 µg/ml, respectively.

Figure 3:
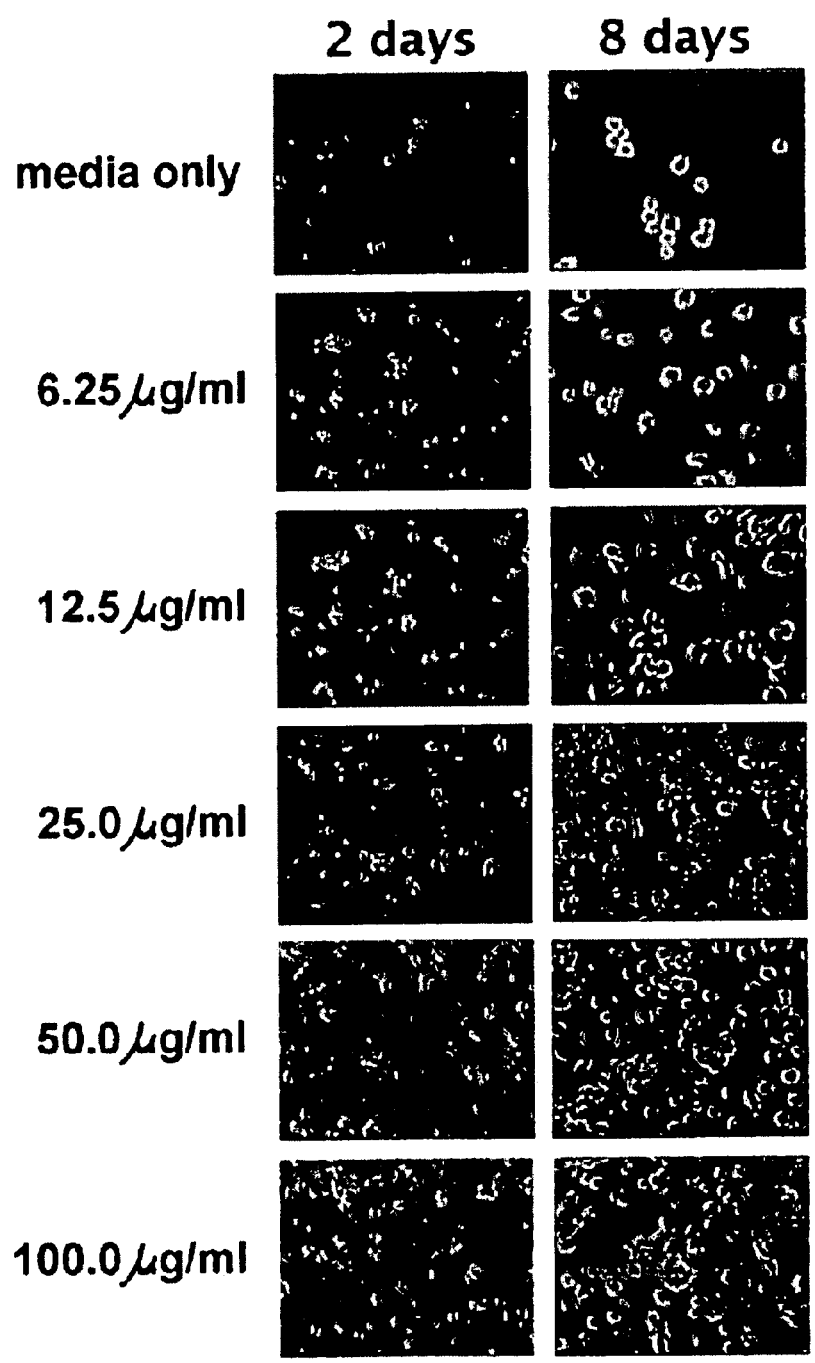
FIG. 3: Phase contrast microscopy of PBMC exposed to varying concentrations of pine cone extracts of method 1.

The cells are cultivated for up to 8 days at 37° C. in an atmosphere comprising 5% $CO_2$. FIG. 3 shows a typical phase contrast microscopy image of PBMC exposed to varying concentrations of pine cone extracts of method 1. Clearly, a marked increase in cell number roughly proportional to pine cone extract concentration is visible. Furthermore, cell morphology changes from disk shaped PBMC morphology to dendritic cell morphology upon exposure to pine cone extract; this effect is best visible at higher concentrations (12.5–100 µg/ml) and 8 days exposure time, but can already be seen at these concentrations on day 2. No visible differences were detected between PBMC exposed to pine cone extracts of method 1 and PBMC exposed to pine cone extracts of method 2 (images not shown).

EXAMPLE 6

Effects of Cytokines and Pine Cone Extracts on PBMC

This example illustrates the effects on PBMC caused by exposition to cytokines and pine cone extracts.

500 µl of PBMC of example 4 (cell concentration: $2 \times 10^6$ cells/ml) are distributed each into the wells of a first 24 well tissue culture plate (Nunc). Then, to each well 500 µl of augmented RPMI 1640 medium (see example 4) are added, wherein the media samples added comprise (=concentrations in media added, not final concentrations!) either no extra substances, 200 µg/ml GM-CSF, 20 ng/ml IL-4, 20 ng/ml TNFα or 200 µg/ml PCE of method 1. After 72 h (initial cultivation) the non adherent cells are harvested and placed in wells of a second 24 well plate. To each of these wells 500 µl of augmented RPMI 1640 medium (see example 4) with pine cone extract of method 1 at a concentration of 200 µg/ml PCE (final concentration 100 µg/ml PCE) is added. After 48 h of cultivation (second cultivation) the non-adherent cells are removed. The adherent cells were washed with PBS (see example 4) and photographed under phase contrast microscopy.

Figure 4:
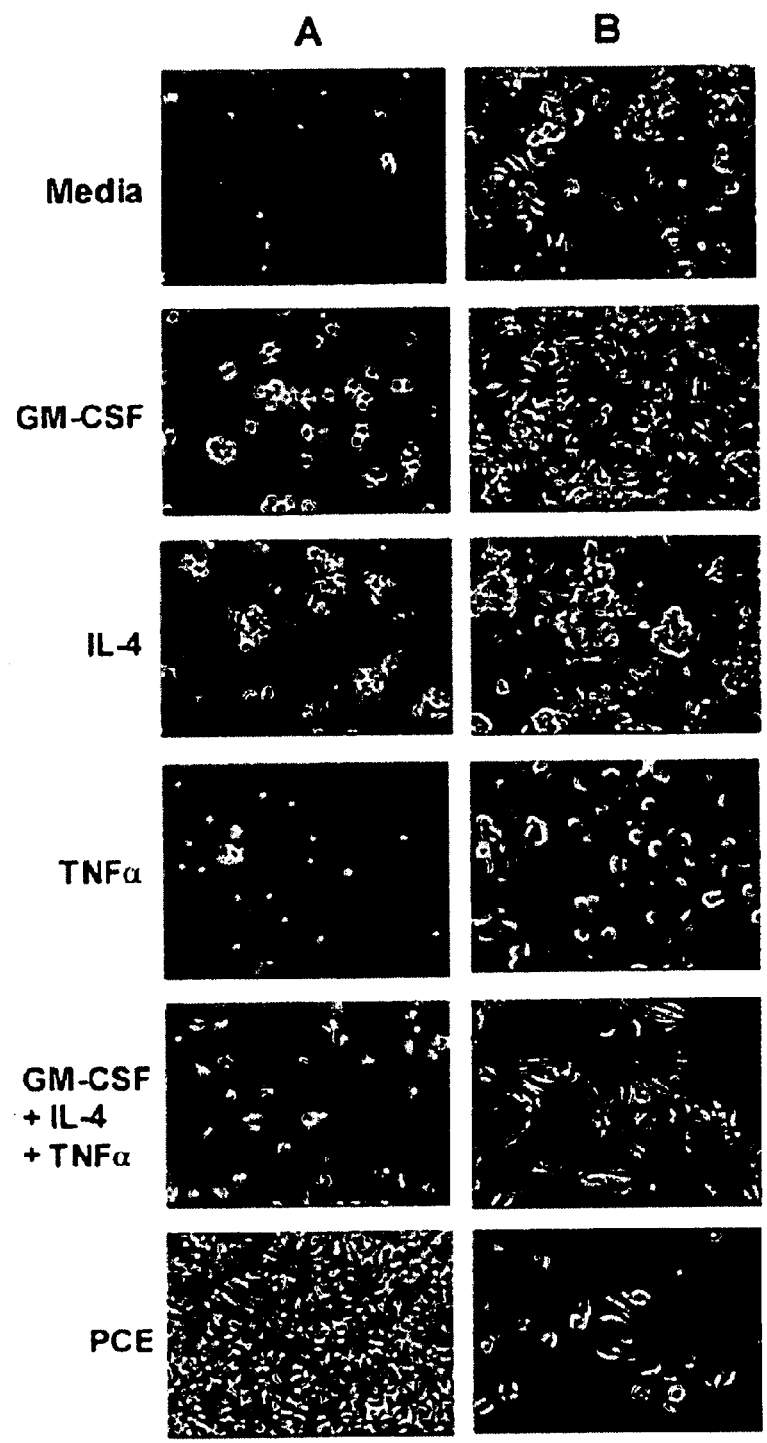
FIG. 4: Phase contrast microscopy of PBMC exposed to cytokines and pine cone extract of method 1.

FIG. 4 shows phase contrast microscopy images of PBMC exposed to the cytokines and pine cone extract of method 1. Images of column A show adherent cells after 72 h of exposure to cytokines or PCE. Images of column B show adherent cells generated by second cultivation from the fraction of non-adherent cells obtained after initial cultivation. The images show that exposition of PBMC to either one of the cytokines tested still allows for a considerable increase in adherent cells by exposure to PCE. They also show that the effect of exposure of PBMC to pine cone extract is similar to that of exposure of PBMC to a cytokine combination known to induce differentiation into dendritic cells. No differences were observed between effects of pine cone extracts of method 1 and pine cone extracts of method 2.

EXAMPLE 7

Generation of Dendritic Cells by Conventional Method

This example illustrates a conventional method of inducing differentiation of PBMC to dendritic cells by exposition to cytokines.

PBMC of example 4 are cultured for 5 days in augmented RMPI 1640 medium (medium definition as in example 4) with additional 100 ng/ml human GM-CSF (R&D Systems, Minneapolis, cat. no. 215-GM-005) and 10 ng/ml IL-4 (R&D Systems, Minneapolis, cat. no. 204-IL-005). Cells are then cultivated for at least 3 days in RMPI 1640 medium as above with additional 10 ng/ml TNFα (R&D Systems, Minneapolis, cat. no. 210-TA-010).

EXAMPLE 8

Detection of Cytokine Production by PBMC Exposed to Pine Cone Extracts

This example illustrates the changes in cytokine production of PBMC caused by exposition to the pine cone extract of method 1.

PBMC are exposed to increasing concentrations of pine cone extract of method 1 as detailed in example 5. Cytokine production is then analyzed by ELISA. ELISAs were performed using the supernatants from 48 hr cultures of PBMC that had been treaed with increasing doses of PCE. The ELISAs to detect the following cytokines, GM-CSR (cat# DGM00), IL-1β (cat#DLB50), IL-6 (cat# D6050), and TNFα (cat# DTA50), were performed according to the manufacturers instructions (R&D Systems, Minneapolis, Minn.). Essentially, 100 µl of the culture supernatant was added to appropriate wells in the 96 well plate provided in the ELISA kit and incubated at room temperature for 2 hours. The wells were washed with the wash buffer provided and then blotted dry. Next, biotinylated antibody specific for the cytokine was added to the well and incubated at room temperature for 2 hours. The wells were washed and blotted dry. Streptavidin-conjugated horseradish peroxidase was added to each well for 20 minutes and then detected using tetramethylbenzidine in hydrogen peroxide as the substrate. After 30 minutes the reaction was terminated by the addition of an acidic solution and the absorbance of the mixture at 450 nm was measured using a plate spectrophotometer (Molecular Devices, Mountainview, Calif.)

Figure 5:
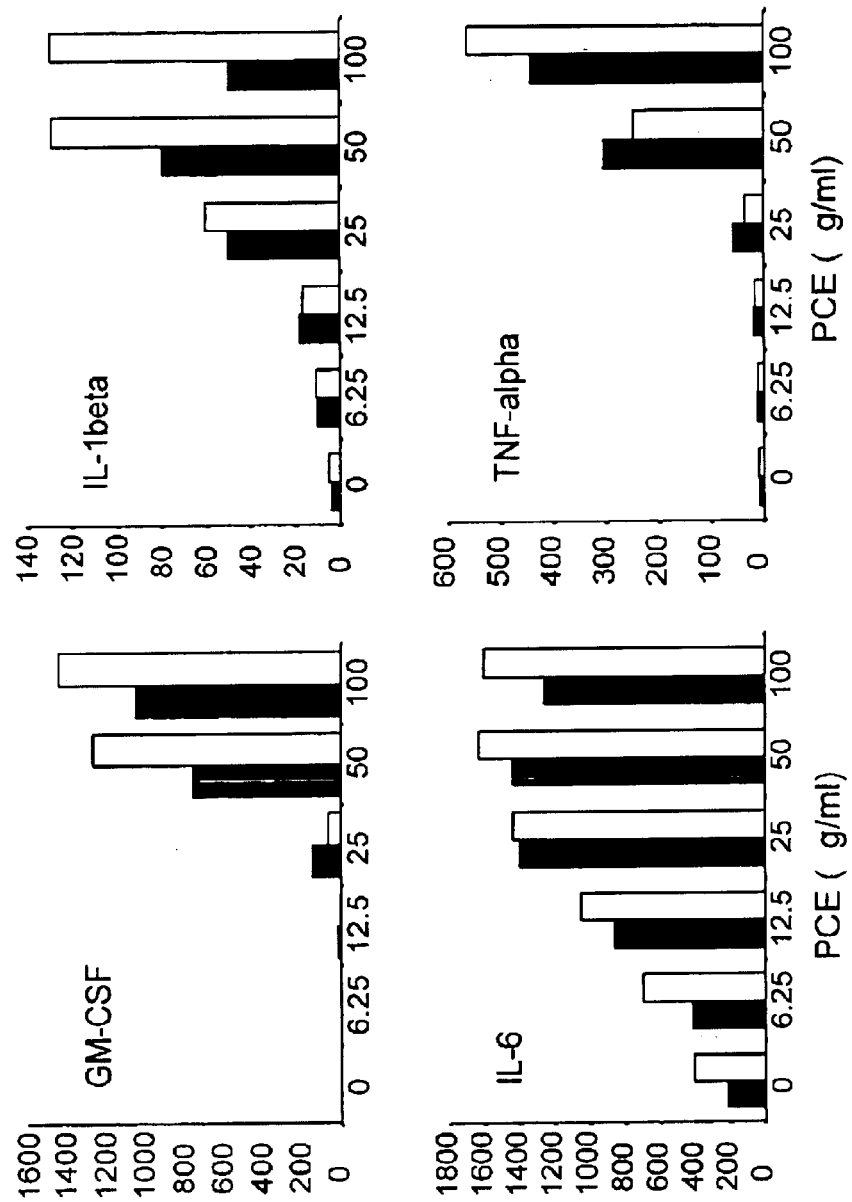
FIG. 5: Pine cone extract induced production of cytokines in cultures of PBMC derived from two different blood donors.

FIG. 5 shows pine cone extract induced production of cytokines in cultures of PBMC derived from two different blood donors. Cytokine production data of one donor is consistently given in black bars, whereas data of the other donor is given in light bars. The diagrams show pine cone induced production of GM-CSF (upper left diagram), IL-1β (upper right diagram), IL-6 (lower left diagram) and TNFα (lower right diagram). Final pine cone extract concentration in the cultivation media is given in µg/ml. The diagrams show a general increase in cytokine production roughly proportional to pine cone extract concentration during exposure. The inventors could not detect IL-4 or IL-10 in the media (data not shown). No differences in cytokine expression were observed between cells exposed to pine cone extracts of method 1 and cells exposed to pine cone extracts of method 2.

EXAMPLE 9

Activation of Naïve Allogeneic T Cells by $CD14^+$ Cells Exposed to Pine Cone Extracts This example illustrates the ability of $CD14^+$ having been exposed to pine cone extracts of method 1 to activate naïve allogeneic $CD3^+$ cells.

A pure population of phenotypically dendritic cells is derived from PBMC of example by extraction with magnetic beads (CD14+ Miltenyi Biotech, Auburn Calif., cat# 502-01) according to the manufacturer's instructions.

The thus isolated CD14+ cells are distributed into the wells of a 6 well tissue culture plate (Nunc) and exposed to augmented RPMI 1640 medium as defined in example 4 with a pine cone extract of method 1 at a final concentration of 100 µg/ml for 8 days. The cells differentiate into phenotypically dendritic cells as described in example 5.

The remaining non-adherent cells are removed. The phenotypically dendritic cells are harvested (see example 5), transferred to fresh augmented RPMI 1640 medium as defined in example 4 and distributed in 100 µl volumes into the wells of a 96 well round bottom tissue culture plate (Nunc) to final varying concentrations of phenotypically dendritic cells per well.

Naïve allogeneic and autologous CD3+ cells are obtained by using CD3+ microbeads (Miltenyi Biotech) according to the manufacturers instructions.

The CD3+ cells are harvested and distributed in augmented RPMI 1640 medium as defined in example 4 in 100 µl volumes to the phenotypically dendritic cells on the second tissue culture plate to a final concentration of $10^5$ CD3+ cells per well. The mixed cells were coincubated for 3 days. After 3 days, concentrations of IFN-gamma are determined by ELISA (R&D Systems, Minneapolis, cat. no. DIF50) according to manufacturer's instructions.

Figure 6:
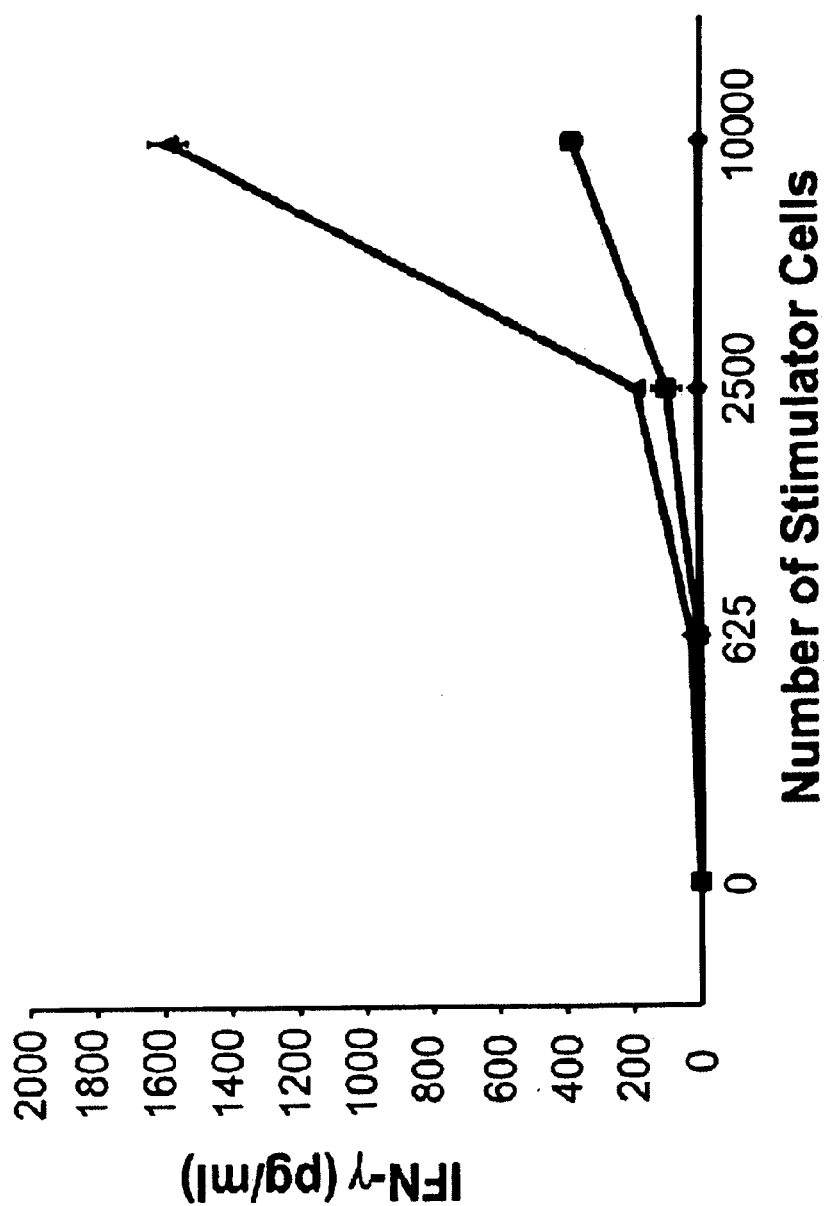
FIG. 6: Interferon gamma production by allogeneic and autologous CD3' cells upon coincubation with varying concentrations of CD14+ cells having been exposed to pine cone extracts of method 1.

FIG. 6 shows IFN-gamma production by allogeneic and autologous CD3+ cells determined after coincubation. Triangles show IFN-gamma concentrations after coincubation of CD3+ cells with dendritic cells that were obtained as described in example 7. Squares show IFN-gamma concentrations after coincubation with phenotypically dendritic cells as described above (prepared in the presence of PCE). Diamonds show IFN-gamma concentrations of CD3+ cells incubated with PBMC exposed to media only. Dendritic cells as obtained by the method described in example 7 are most effective in stimulating IFN-gamma production. Phenotypically dendritic cells obtained by the method described above are significantly more effective in stimulating IFN-gamma production than is medium alone, but are less effective than dendritic cells as obtained by the method of example 7. No significant differences in effect were observed between use of pine cone extracts of method 1 and 2 (data not shown).

It seems that the cells obtained by exposure to pine cone extracts are, though phenotypically dendritic cells, immature and not fully mature dendritic cells.

EXAMPLE 10

Adjuvant Activity of Pine Cone Extract in an HIV DNA (gag) Vaccine Model

This example illustrates the effects of pine cone administration in a DNA vaccination procedure.

Balb/c mice are injected intramuscularly in each quadriceps with 50 µg of vaccine DNA, suspended in 50 µl PBS or suspended in 50 µl of a 40 µg/ml pine cone extract composition of method 1 (coinjection). Vaccine DNA is a plasmid vector expressing HIV gag as immunogen, viz pCIgag. Control DNA is a plasmid vector expressing CAT, viz pCICAT. In another treatment group, Balb/c mice were supplied 200 µg/ml pine cone extract in their drinking water for the duration of the experiment. These mice were also vaccinated with the plasmid vectors as described above.

3 weeks after vaccination, the vaccinated mice are challenged with an intravenous injection of $3 \times 10^6$ pfu of a vaccinia expression vector expressing HIV gag. 3 days after this challenge, the mice are killed, their spleens are harvested and their splenocytes are isolated by common techniques, see Bradley, W. G., Ogata, N., Good, R. A., and N. K. Day; "AlteratiO of in vivo cytokine gene expression in mice infected with a molecular clone of the defective MAIDS virus", 1994, J. Acquired Immune Deficiency Syndromes. 7:1–9.

The splenocytes are washed with PBS (see example 5), pelleted by low speed centrifugation and then suspended in ice cold PBS containing 2% w/w heat inactivated fetal calf serum and placed on ice for 15 min. Then, the appropriate antibodies recognizing CD4+ or CD8+ and IFN-gamma are added to the cells. Cells and antibodies are incubated for 30 min on ice in the dark to label the cells. The cells are then washed with ice cold PBS. The washed cells are fixed in 1 ml freshly prepared 1% w/w aqueous paraformaldehyde. The labeled and fixed cells are analyzed for antigen expression using a Becton Dickinson FACS Caliber flow cytometer. A minimum of 10,000 events is collected for analysis.

Figure 7:
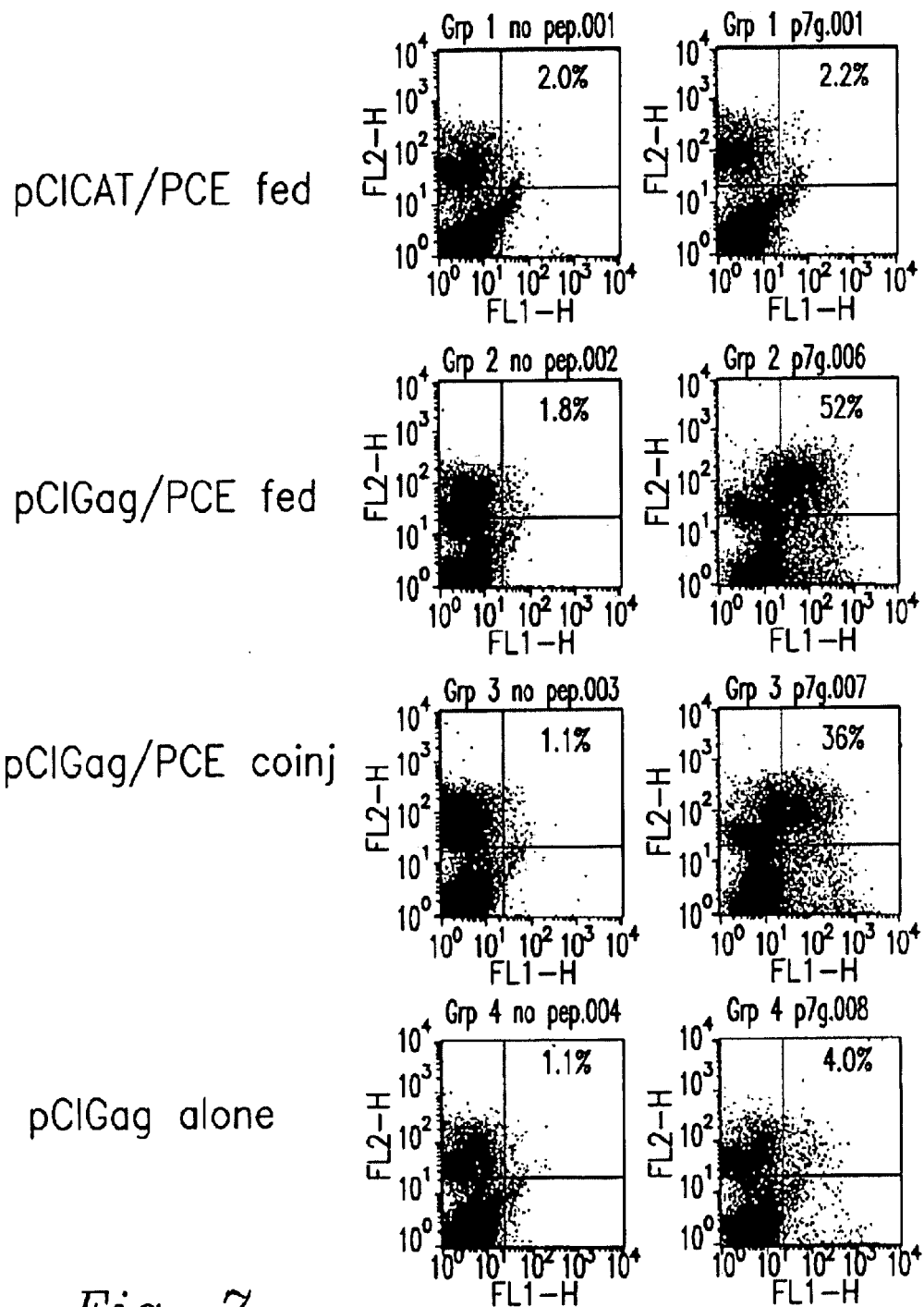
FIGS. 7 and 7a: Adjuvant effects of pine cone extracts on intracellular IFN-gamma production by CD8+ and CD4+ splenocytes of animals vaccinated with DNA vaccines.
Figure 7A:
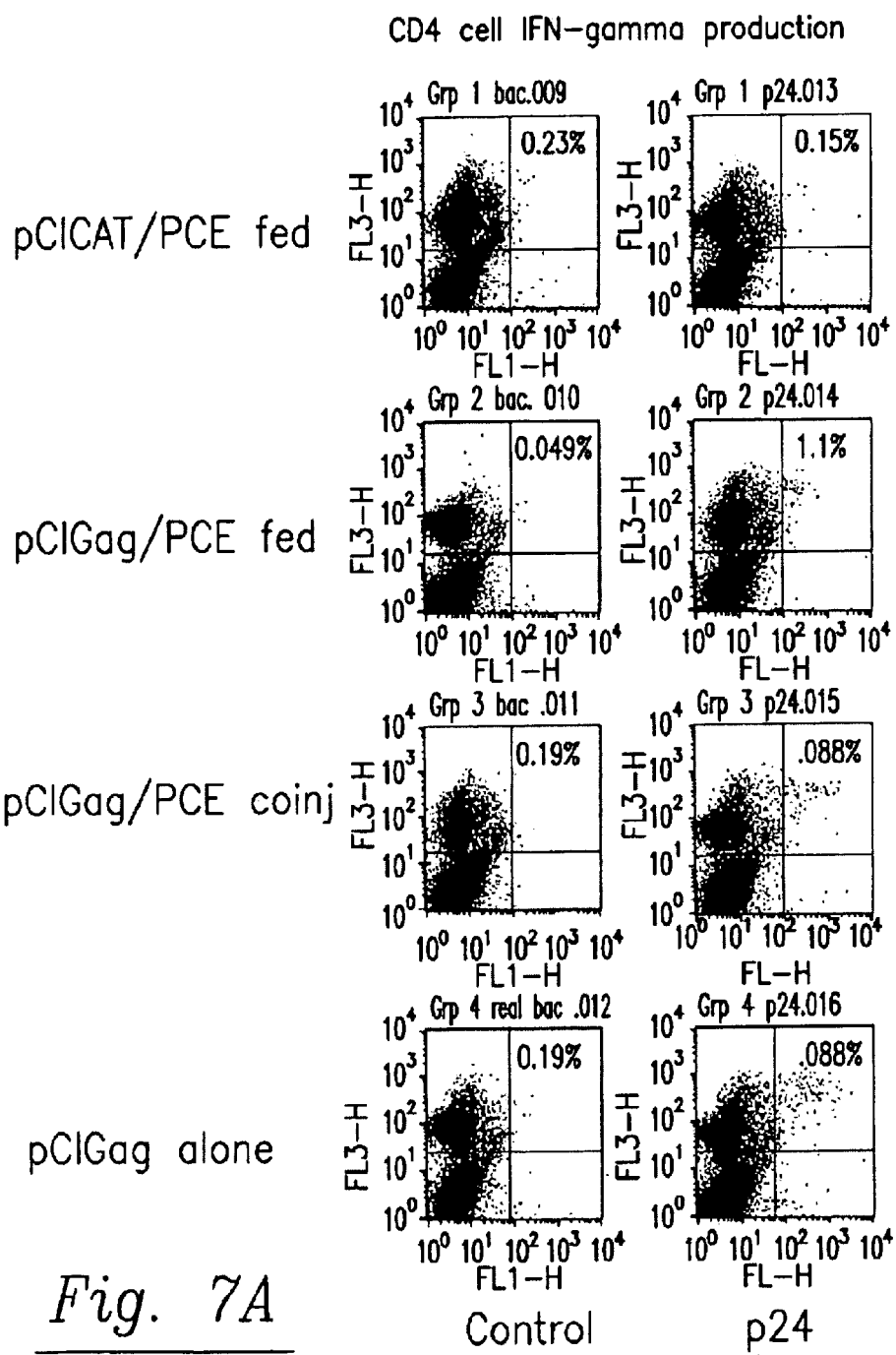

FIGS. 7 and 7a shows the effect of pine cone administration on vaccination effects measured by IFN-gamma production by murine CD8+ and CD4+ splenocytes. The peptide portion of HIV p7g is a stimulant that T cells recognize, specifically CD8+ T cells. Recombinant p24=gag=whole gag protein is the stimulant and is recognized by CD4+ T cells. The response to p24 is optimal for CD4+ T cells. The data show that both oral and intramuscular administration of pine cone extracts during or immediately after vaccination with a nucleic acid vaccine enhances the activation of CD8+ cells (panels "pCIGag/PCE fed" and "pCIGag/PCE coinj"). The enhancement is significantly stronger than for vaccine (pCIGag) administered without pine cone extract adjuvant (panel "pCIGag alone") or control "vaccination" DNA (panel "pCICAT/PCE fed"). Again, no significant differences are observed between pine cone extracts obtained according to method 1 and method 2.

Therefore, the foregoing is considered as illustrative only of the principles of the invention. It is not intended to be exhaustive or to limit the invention to the precise forms disclosed. Obvious modifications or variations are possible in light of the above teachings. All such modifications and variations are within the scope of the invention as determined by the appended claims when interpreted in accordance with the breadth to which they are fairly, legally, equitably entitled.

What is claimed is:

1. A system for vaccination and/or therapy, consisting of a composition or a kit comprising a) a vaccine and b) an adjuvant, wherein the adjuvant comprises a pine cone extract obtained by extraction of pine cone with a solution of potassium hydroxide, and wherein said extract comprises potassium.

2. The system of claim 1, wherein the vaccine is a nucleic acid vaccine.

3. A method of vaccinating or treating a vertebrate, comprising the steps of:
   a) administering to the vertebrate a vaccine; and
   b) administering to the vertebrate a pine cone extract, wherein the administration of said extract is before, during, simultaneously with, or after, the administration of said vaccine, wherein said extract is obtained by extraction of pine cone with a solution of potassium hydroxide, and wherein said extract comprises potassium.

4. The method of claim 3, wherein the vaccine is a nucleic acid vaccine.

5. The method of claim 3, wherein the pine cone extract is administered orally, by intramuscular injection, by inhalation or by application on mucosal skin.

6. The method of claim 3, wherein the vertebrate is vaccinated or treated against cancer and/or viral infection.

7. An adjuvant for administration before, during, simultaneously with, or after, a vaccine, wherein said adjuvant comprises a pine cone extract obtained by extraction of said pine cone with a solution of potassium hydroxide, and wherein said extract comprises potassium.

8. The adjuvant of claim 7, wherein said vaccine is a nucleic acid vaccine.

9. A system for vaccination and/or therapy, consisting of a composition or a kit comprising a) a vaccine and b) an adjuvant, wherein the adjuvant comprises a pine cone extract produced by a method comprising the steps of:
   a) heat extracting defatted ground pine cone material with an aqueous solvent comprising potassium hydroxide;
   b) removing particulate matter with an average particle size greater than 0.2 µm and leaving an aqueous solution; and
   c) adjusting the pH of the resulting aqueous solution to between 6.0 and 8.0.

10. The system of claim 9, wherein the vaccine is a nucleic acid vaccine.

11. The system of claim 9, wherein the pine cone extract is produced by a method further comprising, after said step (c), the steps of:
   (d) filtrating the aqueous solution of step (c) to obtain a retentate fraction;
   (e) drawing off the retentate fraction and removing particles with an average molecular mass of less than 30 kDa; and
   (f) suspending the retentate fraction in an aqueous solvent comprising potassium hydroxide at a pH between 6.0 and 8.0.

12. A method of vaccinating or treating a vertebrate, comprising the steps of:
   a) administering to the vertebrate a vaccine; and
   b) administering to the vertebrate a pine cone extract, wherein the administration of said extract is before, during, simultaneously with, or after, the administration of said vaccine, and wherein said extract is produced by a method comprising the steps of:
   i) heat extracting a defatted ground pine cone material with an aqueous solvent comprising potassium hydroxide;
   ii) removing particulate matter with an average particle size greater than 0.2 µm and leaving an aqueous solution; and
   iii) adjusting the pH of the resulting aqueous solution to between 6.0 and 8.0.

13. The method of claim 12, wherein the vaccine is a nucleic acid vaccine.

14. The method of claim 12, wherein the pine cone extract is administered orally, by intramuscular injection, by inhalation or by application on mucosal skin.

15. The method of claim 12, wherein the vertebrate is vaccinated or treated against cancer and/or viral infection.

16. An adjuvant for administration before, during, simultaneously with, or after, a vaccine, wherein said adjuvant comprises a pine cone extract produced by a method comprising the steps of:
   i) heat extracting a defatted ground pine cone material with an aqueous solvent comprising potassium hydroxide;
   ii) removing particulate matter with an average particle size greater than 0.2 µm and leaving an aqueous solution; and
   iii) adjusting the pH of the resulting aqueous solution to between 6.0 and 8.0.

17. The method of claim 16, wherein the vaccine is a nucleic acid vaccine.

18. A pine cone extract obtained by extraction of a pine cone with a solution of potassium hydroxide, whereby said extract comprises potassium.

19. A pine cone extract produced by a method comprising the steps of:
   i) heat extracting a defatted ground pine cone material with an aqueous solvent comprising potassium hydroxide;
   ii) removing particulate matter with an average particle size greater than 0.2 µm and leaving an aqueous solution; and
   iii) adjusting the pH of the resulting aqueous solution to between 6.0 and 8.0.

* * * * *